United States Patent
Martin

(10) Patent No.: US 8,029,827 B2
(45) Date of Patent: Oct. 4, 2011

(54) INSECTICIDAL COMPOSITIONS SUITABLE FOR USE IN PREPARATION OF INSECTICIDAL LIQUID FERTILIZERS

(75) Inventor: Timothy Martin, Ringoes, NJ (US)

(73) Assignee: FMC Corporation, Philadelphia, PA (US)

( * ) Notice: Subject to any disclaimer, the term of this patent is extended or adjusted under 35 U.S.C. 154(b) by 537 days.

(21) Appl. No.: 11/914,485

(22) PCT Filed: May 11, 2006

(86) PCT No.: PCT/US2006/018224
§ 371 (c)(1),
(2), (4) Date: Nov. 15, 2007

(87) PCT Pub. No.: WO2006/124508
PCT Pub. Date: Nov. 23, 2006

(65) Prior Publication Data
US 2008/0206361 A1    Aug. 28, 2008

Related U.S. Application Data

(60) Provisional application No. 60/682,502, filed on May 19, 2005.

(51) Int. Cl.
*A01N 59/06* (2006.01)
*A01N 65/00* (2006.01)
*A61K 33/12* (2006.01)
(52) U.S. Cl. .......................... 424/683; 514/65
(58) Field of Classification Search .................... 514/65; 424/683
See application file for complete search history.

(56) References Cited

U.S. PATENT DOCUMENTS

| | | | |
|---|---|---|---|
| 5,714,507 A * | 2/1998 | Valcke et al. | 514/383 |
| 5,834,006 A * | 11/1998 | Smith et al. | 424/409 |
| 5,834,400 A * | 11/1998 | Narayanan et al. | 504/363 |
| 7,235,571 B2 * | 6/2007 | Beckmann et al. | 514/355 |

* cited by examiner

*Primary Examiner* — Richard Schnizer
*Assistant Examiner* — Audrea Buckley

(57) ABSTRACT

Insecticidal compositions suitable for use in preparation of insecticidal liquid fertilizers comprising a pyrethroid, a hydrated aluminum-magnesium silicate, and at least one dispersant selected from the group consisting of a sucrose ester, a lignosulfonate, an alkylpolyglycoside, a naphthalenesulfonic acid formaldehyde condensate and a phosphate ester are disclosed.

1 Claim, No Drawings

INSECTICIDAL COMPOSITIONS SUITABLE FOR USE IN PREPARATION OF INSECTICIDAL LIQUID FERTILIZERS

This application claims the benefit of U.S. Provisional Application No. 60/682,502, filed May 19, 2005.

FIELD OF THE INVENTION

The present invention relates to the field of chemical compositions and formulations. In particular, the invention provides an insecticidal composition suitable for use in preparation of insecticidal liquid fertilizers.

BACKGROUND OF THE INVENTION

To enable the efficient elimination or control of unwanted insects in combination with providing nutrients for plants to combat adverse environmental conditions (heat, dry weather, physical contact with animals) it is desirable to formulate an effective chemical insecticide for use in preparation of insecticidal liquid fertilizers. Formulations of insecticides combined with fertilizers are desirable in agricultural and related endeavors due to the multiple benefits conveyed by just one application in a single piece of equipment. One application of such a combination or formulation provides nutrients for the plant growth, while eliminating or controlling unwanted insects that can also affect the health and vitality of the desirable plants.

Mixtures containing insecticide compositions and liquid fertilizers have been practiced in the art, but problems with the physical stability of such mixtures have caused application and efficacy issues. When a traditional insecticidal composition is combined with a liquid fertilizer, the combined components (surfactants, viscosity modifiers, wetting agents) of both may cause accelerated physical degradation (phase separation) of the mixture. This physical degradation can occur in the mix tanks prior to application on the plants. Often this problem goes unnoticed and results in inconsistent application of both the fertilizer and insecticide, yielding inadequate efficacy of both.

SUMMARY OF THE INVENTION

In accordance with the present invention, it has now been found that a new insecticidal composition significantly improves physical stability when used to prepare an insecticidal liquid fertilizer. Specifically, the present invention is directed to an insecticidal composition comprising a pyrethroid, a hydrated aluminum-magnesium silicate, and at least one dispersant selected from the group consisting of a sucrose ester, a lignosulfonate, an alkylpolyglycoside, a naphthalenesulfonic acid formaldehyde condensate and a phosphate ester.

DETAILED DESCRIPTION OF THE INVENTION

The present invention is directed to an insecticidal composition comprising a pyrethroid, a hydrated aluminum-magnesium silicate, and at least one dispersant selected from the group consisting of a sucrose ester, a lignosulfonate, an alkylpolyglycoside, a naphthalenesulfonic acid formaldehyde condensate and a phosphate ester. The dispersant or dispersants are preferably present in a total concentration of from 0.02% by weight to 15% by weight based upon the total weight of all components in the composition.

The pyrethroid is preferably selected from the group consisting of bifenthrin, zeta-cypermethrin, beta-cypermethrin, cypermethrin, deltamethrin, permethrin, lambda-cyhalothrin, gamma-cyhalothrin, tralomethrin, cyfluthrin, beta-cyfluthrin, esfenvalerate, fluvalinate and natural pyrethrum; more particularly, the pyrethroid is bifenthrin. The pyrethroid is preferably present in a concentration of from 1.0% by weight to 25% by weight, more particularly, from 15% by weight to 25% by weight based upon the total weight of all components in the composition.

The hydrated aluminum-magnesium silicate is preferably selected from the group consisting of montmorillonite and attapulgite. The phosphate ester dispersant is preferably selected from the group consisting of a nonyl phenol phosphate ester and a tridecyl alcohol ethoxylated phosphate potassium salt.

The composition may further comprise at least one of an anti-freeze agent, an anti-foam agent and a biocide.

The composition may further comprise an insecticidally effective amount of one or more additional insecticides. Preferred insecticides are selected from the group consisting of imidacloprid, flonicamid, nithiazine, thiamethoxam, dinotefuran, nitenpyram, thiacloprid, clothianadin and chlorfenapyr.

Another embodiment of the present invention is a composition comprising a pyrethroid, a hydrated aluminum-magnesium silicate, at least one dispersant selected from the group consisting of a sucrose ester, a lignosulfonate, an alkylpolyglycoside, a naphthalenesulfonic acid formaldehyde condensate and a phosphate ester and a liquid fertilizer. The liquid fertilizer is preferably present in a concentration of from 95.00% by weight to 99.99% by weight based upon the total weight of all components in the formulation. The composition may further comprise at least one of an anti-freeze agent, an anti-foam agent and a biocide. The composition may also further comprise an insecticidally effective amount of one or more additional insecticides selected from the group consisting of imidacloprid, flonicamid, nithiazine, thiamethoxam, dinotefuran, nitenpyram, thiacloprid, clothianadin and chlorfenapyr.

An especially preferred embodiment of the present invention is an insecticidal composition comprising from 15% to 25% of bifenthrin, from 1% to 20% of hydrated aluminum-magnesium silicate and from 0.02% to 15% of at least one dispersant selected from the group consisting of a sucrose ester, a lignosulfonate, an alkylpolyglycoside, a naphthalenesulfonic acid formaldehyde condensate and a phosphate ester, wherein all % are % by weight based upon the total weight of all components in the composition.

Another especially preferred embodiment of the present invention is an insecticidal fertilizer composition comprising from 0.75% to 1.25% of bifenthrin, from 0.05% to 1.0% of hydrated aluminum-magnesium silicate, from 0.1% to 0.75% of at least one dispersant selected from the group consisting of a sucrose ester, a lignosulfonate, an alkylpolyglycoside, a naphthalenesulfonic acid formaldehyde condensate and a phosphate ester, and from 95% to 99.99% of a liquid fertilizer, wherein all % are % by weight based upon the total weight of all components in the composition.

The present invention encompasses a method of controlling unwanted insects and providing nutrients to plants, the method comprising applying to an area infested with such insects and containing such plants an effective amount of a liquid fertilizer in combination with one of the compositions of this invention.

The present invention also encompasses a process for preparing a composition of this invention comprising dispersing a pyrethroid in a mixture of water and at least one dispersant; and optionally an anti-freeze agent, an anti-foam agent and a biocide, wet milling the mixture and adding a hydrated aluminum-magnesium silicate. The process may further comprise adding the resultant mixture to a liquid fertilizer.

As used in this specification and unless otherwise indicated the term "insecticide" refers to a molecule or combination of molecules that repels, retards, or kills insects, and can be used for crop protection, edifice protection, turf protection, or protection of a person. The term "liquid fertilizer" refers to a fertilizer in a fluid or liquid form containing various ratios of nitrogen, phosphorous and potassium (for example, but not limited to, 10% nitrogen, 34% phosphorous and 0% potassium) and micronutrients. The term "ambient temperature" as utilized herein shall mean any suitable temperature found in a laboratory or other working environment, and is generally not below about 15° C. nor above about 30° C.

The modifier "about" is used herein to indicate that certain preferred operating ranges, such as ranges for molar ratios for reactants, material amounts, and temperature, are not fixedly determined. The meaning will often be apparent to one of ordinary skill. For example, a recitation of a temperature range of about 120° C. to about 135° C. in reference to, for example, an organic chemical reaction would be interpreted to include other like temperatures that can be expected to favor a useful reaction rate for the reaction, such as 105° C. or 150° C. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

The compositions of the present invention are further illustrated by the examples below. The examples serve only to illustrate the invention and should not be interpreted as limiting since further modifications of the disclosed invention will be apparent to those skilled in the art. All such modifications are deemed to be within the scope of the invention as defined in the claims.

Example 1

This example illustrates the preparation of a composition (Composition A) of the present invention.

An amount of 1,252.01 grams of water was combined with 492.65 grams of propylene glycol, 468.07 grams of tridecyl alcohol ethoxylated phosphate potassium salt (Dextrol OC-180 available from Dexter Chemical Corp. in Bronx, N.Y.), 314.59 grams of $C_9$-$C_{11}$ alkyl d-glucopyranoside (Agnique 9116 available from Cognis Corporation in Cincinnati, Ohio), 17.46 grams of polydimethylsiloxane (DowCorning AF available from Dow Corning Corp. in Midland, Mich.) and 8.74 grams of an isothiazodone compound (Kathon CG/ICP available from Rohn and Haas Co. in Philadelphia, Pa.) and the mixture was agitated. To this mixture was added 9,072.34 grams of bifenthrin (22.90 weight % active ingredient). The resultant mixture was milled to less than 9 microns and then 245.14 grams of attapulgite clay (Attaflow FL available from Englehard in Iselin, N.J.) was added to modify the final viscosity and produce a composition of the present invention.

Example 2

This example illustrates the preparation of a composition (Composition B) of the present invention.

An amount of 1,726.24 grams of water was combined with 269.89 grams of propylene glycol, 154.22 grams of tridecyl alcohol ethoxylated phosphate potassium salt (Dextrol OC-180 available from Dexter Chemical Corp. in Bronx, N.Y.), 269.89 grams of $C_9$-$C_{11}$ alkyl d-glucopyranoside (Agnique 9116 available from Cognis Corporation in Cincinnati, Ohio), 7.71 grams of polydimethylsiloxane (DowCorning AF available from Dow Corning Corp. in Midland, Mich.) and 3.86 grams of an isothiazodone compound (Kathon CG/ICP available from Rohn and Haas Co. in Philadelphia, Pa.) and the mixture was agitated. To this mixture was added 922.51 grams of bifenthrin (94.60 weight % active ingredient). The resultant mixture was milled to less than 9 microns and then 501.22 grams of attapulgite clay (Attaflow FL available from Englehard in Iselin, N.J.) was added to modify the final viscosity and produce a composition of the present invention.

Example 3

This example illustrates the preparation of a composition (Composition C) of the present invention.

An amount of 170.80 grams of water was combined with 24.0 grams of propylene glycol, 12.0 grams of tridecyl alcohol ethoxylated phosphate potassium salt (Dextrol OC-180 available from Dexter Chemical Corp. in Bronx, N.Y.), 12.0 grams of $C_9$-$C_{11}$ alkyl d-glucopyranoside (Agnique 9116 available from Cognis Corporation in Cincinnati, Ohio), 12.0 grams of naphthalenesulfonic acid formaldehyde condensate (Agnique ANSC 1NP available from Cognis Corporation in Cincinnati, Ohio), 0.80 gram of polydimethylsiloxane (DowCorning AF available from Dow Corning Corp. in Midland, Mich.) and 0.40 gram of an isothiazodone compound (Kathon CG/ICP available from Rohn and Haas Co. in Philadelphia, Pa.) and the mixture was agitated. To this mixture was added 96.0 grams of bifenthrin (94.60 weight % active ingredient). The resultant mixture was milled to less than 9 microns and then 72.0 grams of attapulgite clay (Attaflow FL available from Englehard in Iselin, N.J.) was added to modify the final viscosity and produce a composition of the present invention.

Example 4

This example illustrates the preparation of a composition (Composition D) of the present invention.

An amount of 178.8 grams of water was combined with 24.0 grams of propylene glycol, 28.0 grams of $C_9$-$C_{11}$, alkyl d-glucopyranoside (Agnique 9116 available from Cognis Corporation in Cincinnati, Ohio), 0.80 gram of polydimethylsiloxane (DowCorning AF available from Dow Corning Corp. in Midland, Mich.) and 0.40 gram of an isothiazodone compound (Kathon CG/ICP available from Rohn and Haas Co. in Philadelphia, Pa.) and the mixture was agitated. To this mixture was added 96.0 grams of bifenthrin (94.60 weight % active ingredient). The resultant mixture was milled to less than 9 microns and then 72.0 grams of attapulgite clay (Attaflow FL available from Englehard in Iselin, N.J.) was added to modify the final viscosity and produce a composition of the present invention.

Example 5

Comparative Stability Studies

This example sets forth stability studies that were performed on compositions prepared in accordance with the present invention.

The physical stability of Composition D of Example 4 was tested by mixing the composition with a 10% nitrogen-34% phosphorous-0% potassium liquid fertilizer at a 1% active ingredient ratio and observing the mixture's physical stability in a 500 milliliter/50 cm column. Composition D's stability was compared with that of a traditional composition in the art, an Emulsifiable Concentrate (EC) of bifenthrin that was mixed at a 1% active ingredient ratio with a 10-34-0 liquid fertilizer. As phase separation of the mixtures occurred at 0, 20, 40 60 and 100 minutes, the bottom layer was removed and analyzed for weight % bifenthrin to determine the remaining amount of bifenthrin in the column. Table 1 contains the results of the stability test.

TABLE 1

Physical Stability
% of Total Bifenthrin Remaining in Mixture Over Time

| | Time (minutes) | | | | |
|---|---|---|---|---|---|
| | 0 | 20 | 40 | 60 | 100 |
| Composition D | 100 | 92 | 93 | — | 96 |
| Bifenthrin EC | 100 | 12 | 6 | 3 | 1 |

While this invention has been described with an emphasis upon preferred embodiments, it will be obvious to those of ordinary skill in the art that variations in the preferred compositions and methods may be used and that it is intended that the invention may be practiced otherwise than as specifically described herein. Accordingly, this invention includes all modifications encompassed within the spirit and scope of the invention as defined by the claims that follow.

What is claimed is:

1. A composition consisting essentially of
  a) from 15% to 25% of bifenthrin;
  b) from 1% to 20% of hydrated aluminum-magnesium silicate; and
  c) from 0.02% to 15% of at least one dispersant selected from the group consisting of a sucrose ester, a lignosulfonate, an alkylpolyglycoside, a naphthalenesulfonic acid formaldehyde condensate and a phosphate ester;

wherein all % are % by weight based upon the total weight of all components in the composition.

* * * * *